(12) United States Patent
Ragsdale

(10) Patent No.: US 6,171,282 B1
(45) Date of Patent: Jan. 9, 2001

(54) SOFT CANNULA AND METHODS FOR USE

(76) Inventor: Edgar K. Ragsdale, 3216 SE. Biddle Rd., Vancouver, WA (US) 98683

( * ) Notice: Under 35 U.S.C. 154(b), the term of this patent shall be extended for 0 days.

(21) Appl. No.: 09/361,018

(22) Filed: Jul. 23, 1999

(51) Int. Cl.[7] .................................................... A61M 5/00
(52) U.S. Cl. .................. 604/171; 604/175; 604/164.11; 604/506; 604/264
(58) Field of Search .................................... 604/171, 174, 604/175, 159, 161, 164, 528, 506, 95, 264, 165

(56) References Cited

U.S. PATENT DOCUMENTS

| | | |
|---|---|---|
| 5,151,105 | 9/1992 | Kwan-Gett . |
| 5,257,980 * | 11/1993 | Van Antwerp et al. ............. 604/282 |
| 5,320,611 | 6/1994 | Bonutti et al. . |
| 5,391,156 * | 2/1995 | Hildwein et al. ................... 604/174 |
| 5,573,517 | 11/1996 | Bonutti et al. . |
| 5,730,724 * | 3/1998 | Plishka et al. ......................... 604/95 |
| 5,766,220 | 6/1998 | Moenning . |
| 5,947,940 * | 9/1999 | Beisel .................................. 604/282 |

* cited by examiner

Primary Examiner—Sharon Kennedy
Assistant Examiner—Michael J. Hayes
(74) Attorney, Agent, or Firm—Miller Nash LLP

(57) ABSTRACT

A soft cannula including a flexible exosheath having a flexible, shape retainable annular member attached at one end. In one preferred embodiment the soft cannula includes a retrieval suture attached to the annular member. One end of the soft cannula is positioned within the patient's body cavity so that medical instruments may be inserted into the other and giving access to the patient's body cavity. The present invention also includes at least two preferred methods for inserting the soft cannula.

12 Claims, 3 Drawing Sheets

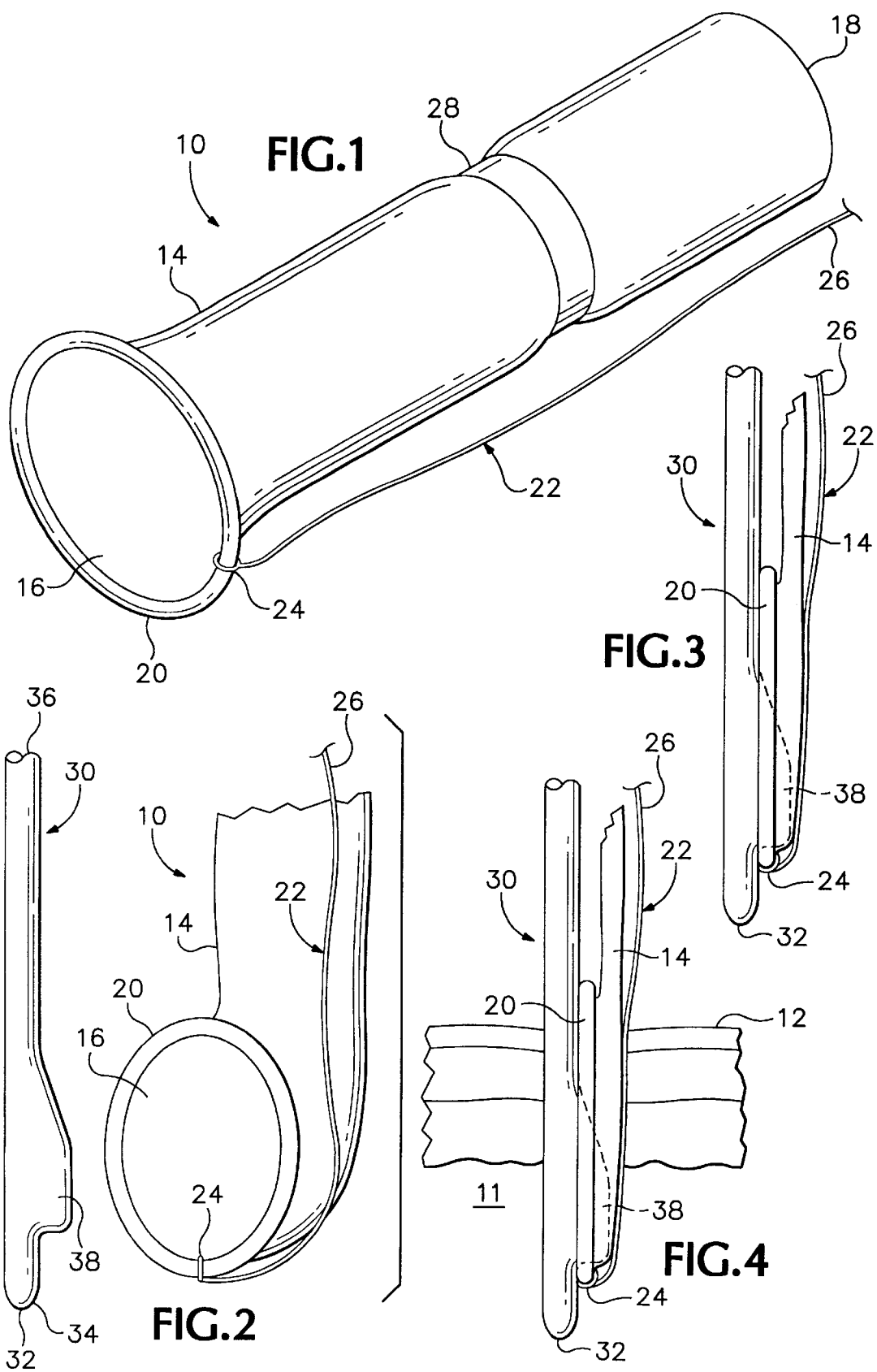

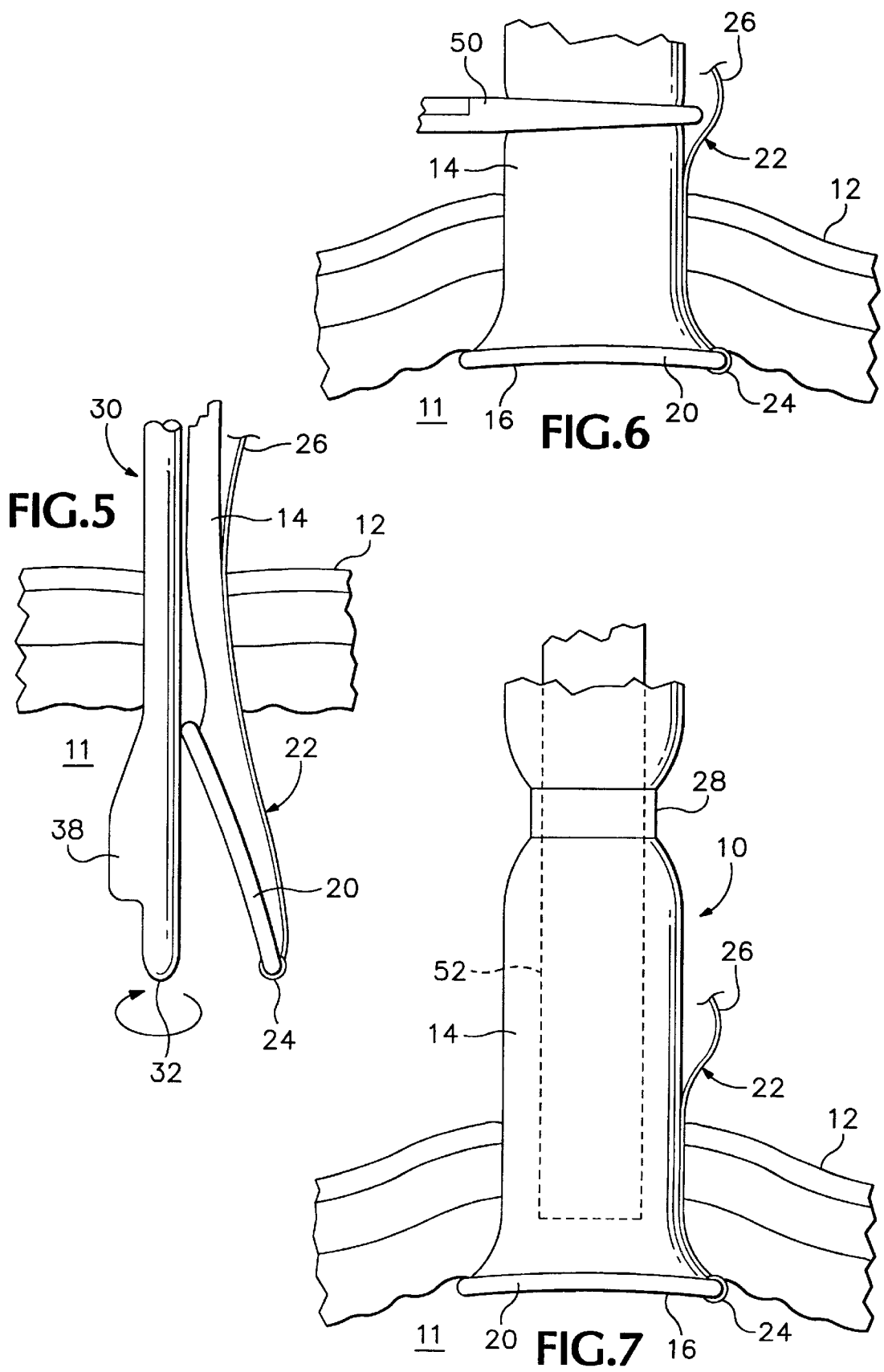

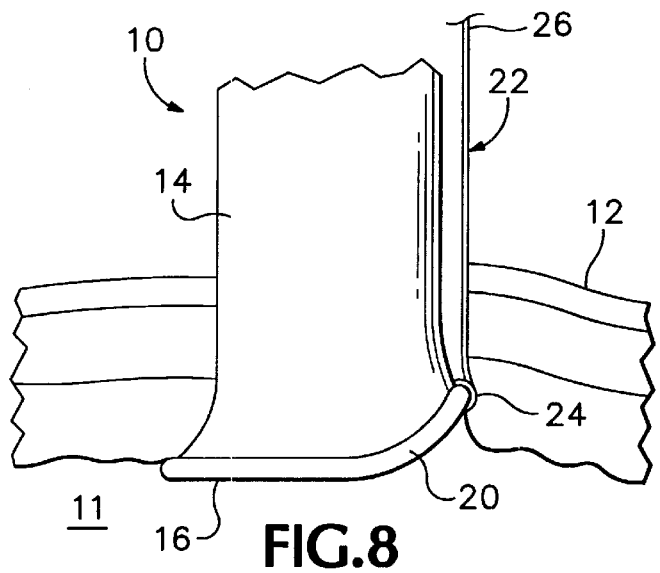
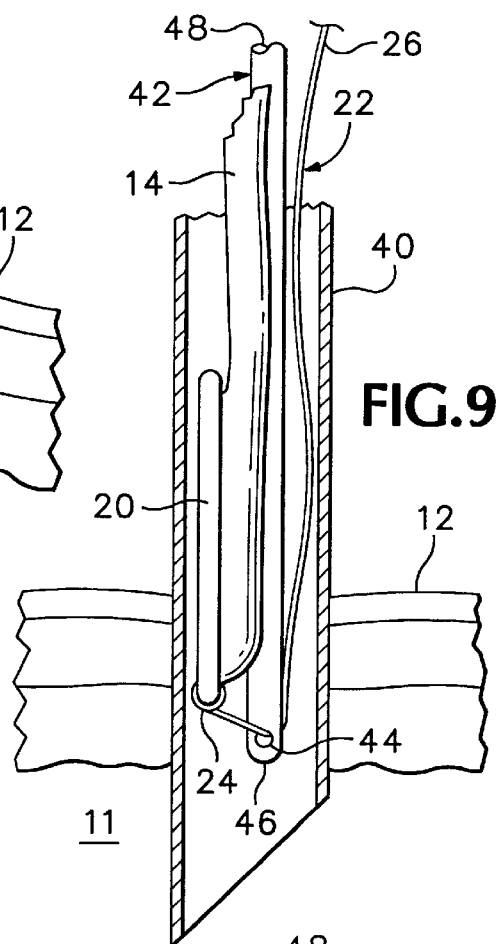
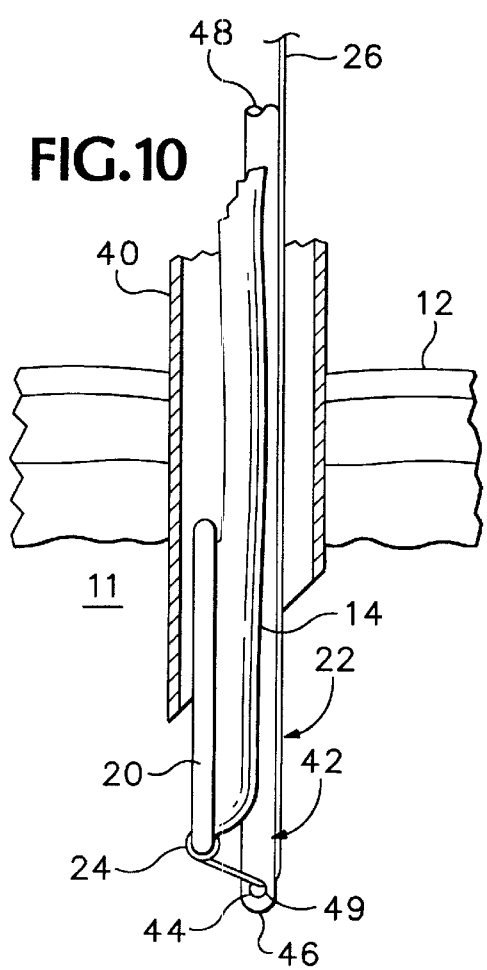
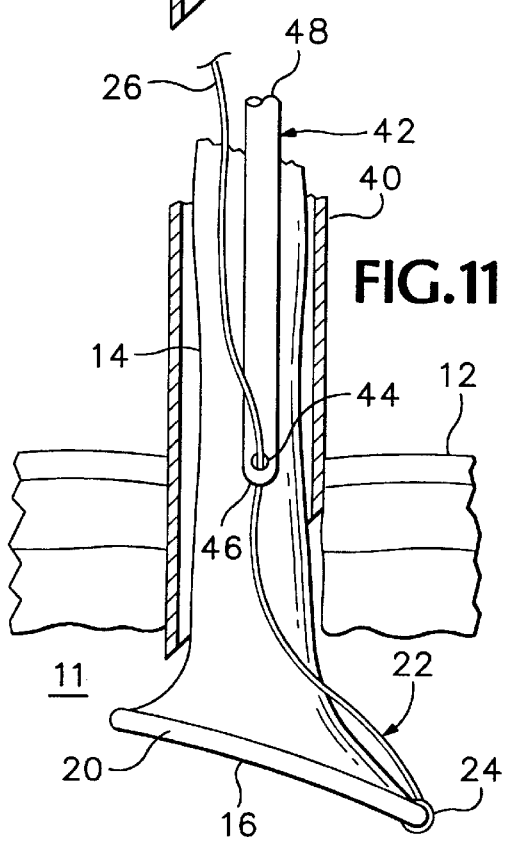

SOFT CANNULA AND METHODS FOR USE

BACKGROUND OF THE INVENTION

The present invention relates to a soft cannula and methods for insertion into, removal from, and use within a patient's body cavity.

During many types of arthroscopic operations a rigid cannula is inserted into a patients body to provide access for medical instruments. The rigidity of the cannula creates several problems: large insertion points are generally required to accommodate the circumference of the rigid cannula; the circumference available for manipulating the instruments is strictly limited; the gasket or ribbing on the outer circumference of the cannula provides very little traction; and apparatus for sealing the cannula tends to leak.

U.S. Pat. No. 5,573,517 and U.S. Pat. No. 5,532,611 (the "Bonutti et al. references") are directed to cannulas that are inserted through tissue in an unexpanded condition. Once inserted, the inserted cannula is expanded radially to allow for instrument passage. Each Bonutti et al. cannula uses a plurality of wires or longitudinally extending members that extend through the length of the of the cannula to expand an elastic sheath. To use a Bonutti et al. cannula, a narrow trocar is inserted into the cannula which are then jointly inserted into a small incision in the patient's epidermis. A small tubular insert is then inserted between the cannula and the trocar to expand the cannula radially and allow the trocar to be removed. Additional tubular inserts of progressively increasing diameters are then inserted into the cannula. A final full sized tube is left in place within the expanded cannula so that medical instruments may be inserted there through. Although the Bonutti et al. cannulas may provide an expanding circumference that allow for a small insertion point, problems such as the strict limitation of the circumference available for manipulating instruments, little traction, and leakage are not addressed. Further, it is questionable as to whether the Bonutti et al. Cannulas are significantly flexible.

BRIEF SUMMARY OF THE INVENTION

The soft cannula of the present invention allows more room for manipulation of surgical instruments, more traction to prevent the cannula from slipping out of its insertion point, can be closed with a standard clamp, and can be sealed with an elastic band or clamp to form a substantially leak proof seal.

More specifically, a cannula of the present invention includes a flexible exosheath having an open body insertion end and an open instrument insertion end. A flexible, shape retainable annular member is preferably annularly attached to the body insertion end of the flexible exosheath. Preferably the cannula also includes a retrieval suture attached to the annular member. The body insertion end is designed to be positioned within a patient's body cavity so that medical instruments may be inserted into the instrument insertion end and thereby have access to the patient's body cavity. The cannula may also include an annular constriction band integral with the flexible exosheath and positioned between the body insertion end and the instrument insertion end.

The present invention also includes two preferred methods of insertion of the soft cannula. One method attaches the soft cannula to an attachment member of an inserter so that both are inserted together into the patient's body cavity. The annular member is then dislodged from the attachment member and the inserter is withdrawn from the patient's body cavity. The second preferred method uses a pre-inserted rigid cannula through which a compressed soft cannula and an alternate inserter are inserted. When the soft cannula is in position, the alternate inserter is removed from the retrieval suture as the inserter is withdrawn, leaving the soft cannula in place.

The foregoing and other objectives, features, and advantages of the invention will be more readily understood upon consideration of the following detailed description of the invention, taken in conjunction with the accompanying drawings.

BRIEF DESCRIPTION OF THE SEVERAL VIEWS OF THE DRAWING

FIG. 1 is a perspective view of a soft cannula of the present invention.

FIG. 2 is a perspective side view of one preferred inserter adjacent a relaxed soft cannula of the present invention.

FIG. 3 is a side view of the soft cannula positioned on the inserter of FIG. 2.

FIG. 4 is a side view of the inserter of FIG. 2, with the soft cannula positioned thereon, partially inserted through a patient's body tissue.

FIG. 5 is a side view of the inserter of FIG. 2 rotated so as to remove the soft cannula.

FIG. 6 is a side view of the soft cannula positioned within a patient's body cavity.

FIG. 7 is a side view of a rigid cannula inserted through the soft cannula positioned within a patient's body cavity.

FIG. 8 is a side view of the soft cannula partially removed from the patient's body cavity.

FIGS. 9–11 are side views of an alternate preferred inserter inserting a soft cannula of the present invention into a patient's body cavity through a pre-inserted rigid cannula.

DETAILED DESCRIPTION OF THE INVENTION

FIG. 1 shows one preferred embodiment of a soft cannula 10 for providing access to a patient's body cavity 11 (FIGS. 4–11) through a patient's integument 12. (For simplicity, the integument 12 will be referred to as body tissue 12, but will include, for example, skin, fat, muscle, and capsule.) The cannula 10 preferably includes a flexible exosheath 14 having an open body insertion end 16 and an open instrument insertion end 18. Preferably, annularly attached to the body insertion end 16 is a flexible, shape retainable annular member 20. When the body insertion end 16 is positioned within the patient's body cavity 11, instruments may be inserted into the instrument insertion end 18 so that a doctor or other medical personal can have access to the patient's body cavity 11.

One of the several advantages of the soft cannula 10 of the present invention is that the flexible exosheath 14 allows medical personnel to have better maneuverability than is available with standard rigid cannulas. Another advantage of the soft cannula 10 of the present invention is that, as will be described below, only a small insertion point is needed in a patient's body tissue 12 to insert the soft cannula 10 because the flexible exosheath 14 and the flexible annular member 20 can be squeezed, rolled, or otherwise constricted before insertion.

The soft cannula 10 preferably further includes a retrieval suture 22 with an attachment end 24 and an exterior retrieval end 26. The attachment end 24 of the retrieval suture 22 is preferably attached to the shape retainable annular member 20 of the soft cannula 10. The retrieval end 26 of the retrieval suture is preferably left outside the patient's body so that it may be pulled to remove the soft cannula 10.

The soft cannula 10 preferably further includes an annular constriction band 28 integral with the flexible exosheath 14 and positioned between the body insertion end 16 and the instrument insertion end 18 of the soft cannula 10. The annular constriction band 28 is particularly suited to preventing leakage of fluids. For example, an instrument inserted into the instrument insertion end 18 would be able to slide through the annular constriction band 28, but would be lightly gripped thereby. The light gripping action of the annular constriction band 28 would tend to prevent fluid in the patient's body from escaping therefrom.

The exosheath 14 may be made of any flexible material including, but not limited to, polyester fillm such as MYLAR™ or aramid yarn such as KEVLAR™. The shape retainable annular member 20 may be made of any shape retainable material including, but not limited to, rubber or nytallium.

FIGS. 2–5 show a series of steps of one preferred method of inserting the soft cannula 10. FIG. 2 shows the soft cannula 10 adjacent to an inserter 30 having a guide point 32 at a first end 34, a second end 36, and an attachment member 38 between the first and second ends 34, 36. The annular member 20 is attached to the attachment member 38 as shown in FIG. 3. Preferably the annular member 20 is attached by stretching the annular member 20 around the attachment member 38. A scalpel is used to cut a small insertion point in the patient's body tissue 12, which is then spread slightly using a hemostat. Next, the inserter 30 and the attached annular member 20 are inserted through the patient's body tissue 12 using the guide point 32 as a guide as shown in FIG. 4. It should be noted that the guide point 32 is shown as relatively dull, and therefore, in this embodiment could require a cut to be made with a sharper instrument such as a scalpel. Alternatively, the guide point 32 could be sharp so that it could both cut and guide simultaneously.

Once the attachment member 38 has cleared the skin, fat, muscle, and capsules of the body tissue 12, the annular member 20 is removed from the attachment member 38. FIG. 5 shows one preferred method for removing the annular member 20 from the attachment member 38. Specifically, the inserter 30 and attachment member 38 are rotated so as to dislodge the annular member 20 from the attachment member 38. Once the annular member 20 has been dislodged, the inserter 30 may be withdrawn from the patient's body cavity 11 while leaving the annular member 20 and the body insertion end 16 of the flexible exosheath 14 within the patient's body cavity 11.

Finally, the annular member 20 may be positioned substantially perpendicular to and forming a seal with the patient's body tissue 12. Specifically, the annular member 20 may be positioned substantially perpendicular to and forming a seal with the patient's body tissue 12 by allowing the annular member 20 to substantially regain its natural shape and then lightly pulling the soft cannula 10 to correctly position the annular member 20. The soft cannula 10 may also be positioned by gently pulling the exterior retrieval end 26 of retrieval suture 22. FIGS. 6 and 7 show a correctly positioned soft cannula.

FIGS. 9–11 show a second preferred method of inserting a soft cannula 10. Specifically, FIG. 9 shows a small rigid cannula 40 that has been inserted into a patient's body cavity 11. Insertion of the small rigid cannula 40 may be accomplished using any standard method. An alternate preferred embodiment of an inserter 42 having a suture attachment member 44 at a first end 46 and a second end 48 distal from the first end 46 is then attached to a soft cannula 10 such as that described above having a flexible, shape retainable annular member 20 with a retrieval suture 22 attached thereto. The shown inserter 42 uses an eye 49 as the suture attachment member 44, however, alternate hooks, grabbing apparatus, or other suitable attachment members could also be used. Preferably the inserter 42 is attached to the soft cannula 10 by attaching the suture attachment member 44 to the retrieval suture 22. Then the annular member 20 is compressed. FIG. 9 shows the compressed annular member 20 and the attached inserter 42 being inserted into the small rigid cannula 40. Then, FIG. 10 shows the inserter 42 being used to guide the compressed annular member 20 through the small rigid cannula 40, through the patient's body tissue 12, and into the patient's body cavity 11.

Once the annular member 20 is beyond the small rigid cannula 40, the suture attachment member 44 may be removed from the retrieval suture 22. The inserter 42 may also be withdrawn from the patient's body cavity 11 while leaving the annular member 20 and the body insertion end 16 of the flexible exosheath 14 within the patient's body cavity 11. FIG. 11 shows the suture attachment member 44 being slid off the retrieval suture 22 as the inserter 42 is withdrawn from within the patient's body cavity 11.

Finally, as discussed above in relation to the first method of inserting the soft cannula, the annular member 20 is preferably positioned substantially perpendicular to and forming a seal with the patient's body tissue 12. Specifically, the annular member 20 may be positioned substantially perpendicular to and forming a seal with the patient's body tissue 12 by allowing the annular member 20 to substantially regain its natural shape and then lightly pulling the soft cannula 10 to correctly position the annular member 20. The soft cannula 10 may also be positioned by gently pulling the exterior retrieval end 26 of retrieval suture 22. FIGS. 6 and 7 show a correctly positioned soft cannula.

The expanded annular member, once in place as shown in FIGS. 6 and 7, provides traction that allows a user to pull the soft cannula 10 slightly upward. This slightly lifts the body tissue 12. This ability helps to widen the joint or other interior body cavity 11, and thus increases working room.

The soft cannula 10 may removed, as shown in FIG. 8, by pulling the exterior retrieval end 26 of the retrieval suture 22. This gently lifts the attached annular member 20 so that it may be removed from the body cavity 11.

An additional advantage of the soft cannula 10 of the present invention over standard rigid cannulas is that it may be sealed to prevent leakage when it is not actually being used. FIG. 6 shows a standard clamp 50 gripping the flexible exosheath 14 so that fluids within the patient cannot escape.

FIG. 7 shows the soft cannula 10 being used in combination with a rigid cannula 52. Such a combination allows levering and prevents the soft cannula 10 from being torn by sharp instruments. However, the flexible exosheath 14 prevents tissue from blocking the orifice.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A method of using a soft cannula, said method comprising the steps of:
   a) providing a soft cannula having a flexible, shape retainable annular member annularly attached to a body insertion end of a flexible exosheath;
   b) providing an inserter having a guide point at a first end, a second end, and a protruding attachment member relative to a surface between said first and second ends;
   c) attaching said annular member to said attachment member by stretching said annular member around said attachment members;
   d) inserting said inserter and said attached annular member into a patient's body cavity;
   e) removing said annular member from said attachment member;
   f) withdrawing said inserter from said patient's body cavity while leaving said annular member and said body insertion end of said flexible exosheath within said patient's body cavity; and
   g) positioning said annular member substantially perpendicular to and forming a seal with interior body tissue of said patient's body cavity.

2. The method of claim 1 wherein said step of removing said annular member from said attachment member further includes the step of rotating said inserter and attachment member so as to dislodge said annular member from said attachment member.

3. The method of claim 1 wherein said step of positioning said annular member further includes the steps of allowing said annular member to substantially regain its natural shape and lightly pulling said soft cannula to correctly position said annular member.

4. The method of claim 1 further including the step of removing said soft cannula by pulling a retrieval suture attached to said annular member.

5. A method of using a soft cannula, said method comprising the steps of:
   a) providing a soft cannula having a flexible, shape retainable annular member annularly attached to a body insertion end of a flexible exosheath;
   b) providing an inserter having a guide point at a first end, a second end, and a protruding attachment member relatives to a surface between said first and second ends;
   c) attaching said annular member to said attachment member;
   d) inserting said inserter and said attached annular member into a patient's body cavity;
   e) removing said annular member from said attachment member by rotating said inserter and attachment member so as to dislodge said annular member from said attachment members;
   f) withdrawing said inserter from said patient's body cavity while leaving said annular member and said body insertion end of said flexible exosheath within said patient's body cavity; and
   g) positioning said annular member substantially perpendicular to and forming a seal with interior body tissue of said patient's body cavity.

6. The method of claim 5 wherein said step of positioning said annular member further includes the steps of allowing said annular member to substantially regain its natural shape and lightly pulling said soft cannula to correctly position said annular member.

7. The method of claim 5 further including the step of removing said soft cannula by pulling a retrieval suture attached to said annular member.

8. A method of using a soft cannula, said method comprising the steps of:
   a) providing a soft cannula having a flexible, shape retainable annular member annularly attached to a body insertion end of a flexible exosheath;
   b) providing an inserter having a guide point at a first end, a second end, and an attachment member between said first and second ends;
   c) attaching said annular member to said attachment member;
   d) inserting said inserter and said attached annular member into a patient's body cavity;
   e) removing said annular member from said attachment member;
   f) withdrawing said inserter from said patient's body cavity while leaving said annular member and said body insertion end of said flexible exosheath within said patient's body cavity;
   g) positioning said annular member substantially perpendicular to and forming a seal with interior body tissue of said patient's body cavity; and
   h) removing said soft cannula by pulling a retrieval suture attached to said annular member.

9. The method of claim 8 wherein said step of positioning said annular member further includes the steps of allowing said annular member to substantially regain its natural shape and lightly pulling said soft cannula to correctly position said annular member.

10. A method of using a soft cannula, said method comprising the steps of:
    a) inserting a small rigid cannula into a patient's body cavity;
    b) providing a soft cannula having a flexible, shape retainable annular member annularly attached to a body insertion end of a flexible exosheath, said annular member having a retrieval suture attached thereto;
    c) providing an inserter having a suture attachment member at a first end and a second end distal from said first end;
    d) attaching said inserter to said soft cannula by attaching said retrieval suture to said suture attachment member;
    e) compressing said annular member;
    f) inserting said compressed annular member and said attached inserter into said small rigid cannula using said inserter to guide said compressed annular member through said small rigid cannula and into said patient's body cavity;
    g) removing said suture attachment member from said retrieval suture and withdrawing said inserter from said patient's body cavity while leaving said annular member and said body insertion end of said flexible exosheath within said patient's body cavity; and
    h) positioning said annular member substantially perpendicular to and forming a seal within said patient's body cavity.

11. The method of claim 10, wherein said step of positioning said annular member substantially perpendicular to and forming a seal within said patient's body cavity further includes the steps of allowing said annular member to substantially regain its natural shape and lightly pulling said soft cannula to correctly position said annular member.

12. The method of claim 10 further including the step of removing said soft cannula by pulling a retrieval suture attached to said annular member.

* * * * *